United States Patent [19]

Komendowski et al.

[11] 4,036,919

[45] July 19, 1977

[54] NEBULIZER-HUMIDIFIER SYSTEM

[75] Inventors: Henry Komendowski, Evanston; Walter Levine, Lincolnwood, both of Ill.

[73] Assignee: Inhalation Therapy Equipment, Inc., Chicago, Ill.

[21] Appl. No.: 641,626

[22] Filed: Dec. 17, 1975

Related U.S. Application Data

[63] Continuation of Ser. No. 483,227, June 26, 1974, abandoned.

[51] Int. Cl.² .................................. A61M 15/00
[52] U.S. Cl. ............................ 261/122; 128/193; 128/194; 261/142; 261/DIG. 65
[58] Field of Search ............... 261/122, 142, DIG. 65; 128/186–188, 192–194, DIG. 2

[56] References Cited

U.S. PATENT DOCUMENTS

| 3,472,425 | 10/1969 | Booth et al. | 261/122 |
| 3,578,295 | 5/1971 | Hudson | 261/122 |
| 3,724,454 | 4/1973 | Brown | 128/194 |
| 3,744,771 | 7/1973 | Deaton | 128/186 |
| 3,746,000 | 7/1973 | Edwards | 128/194 |
| 3,757,082 | 9/1973 | Goicoechea | 261/DIG. 65 |
| 3,771,721 | 11/1973 | Van Amerongen | 128/194 |
| 3,807,445 | 4/1974 | McPhee | 261/DIG. 65 |
| 3,807,713 | 4/1974 | Cornett et al. | 261/122 |

Primary Examiner—Tim R. Miles
Assistant Examiner—Gregory N. Clements
Attorney, Agent, or Firm—Merriam, Marshall, Shapiro & Klose

[57] ABSTRACT

Inhalation therapy devices for vaporizing or nebulizing a liquid into a gas stream including containers having a fluid diffusion chamber disposed at the bottom portion thereof and adapted to receive an element for heating fluids within the diffusion chamber.

12 Claims, 7 Drawing Figures

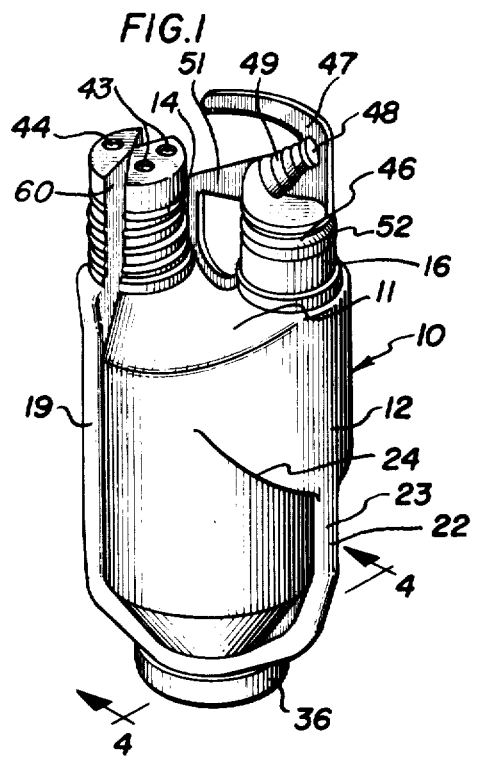
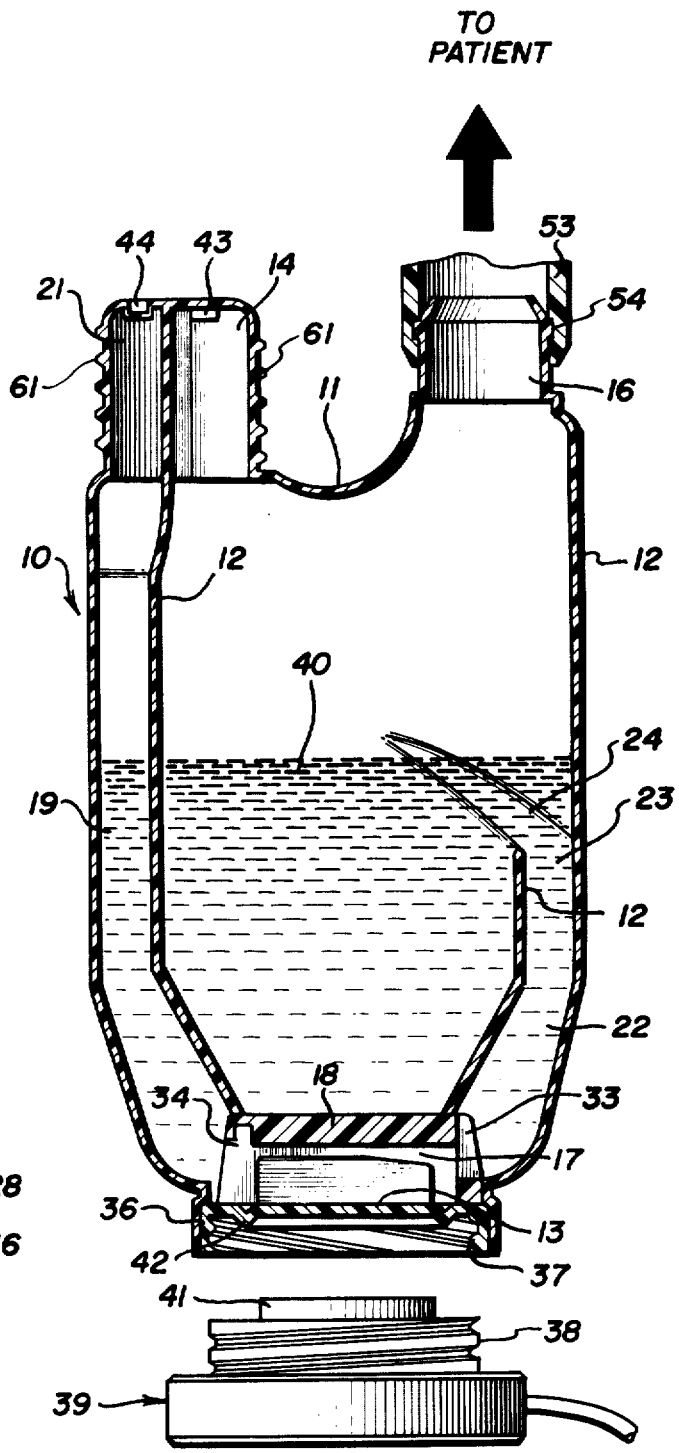

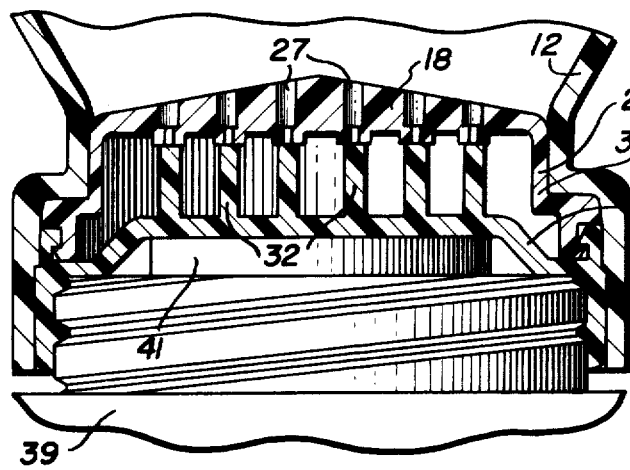
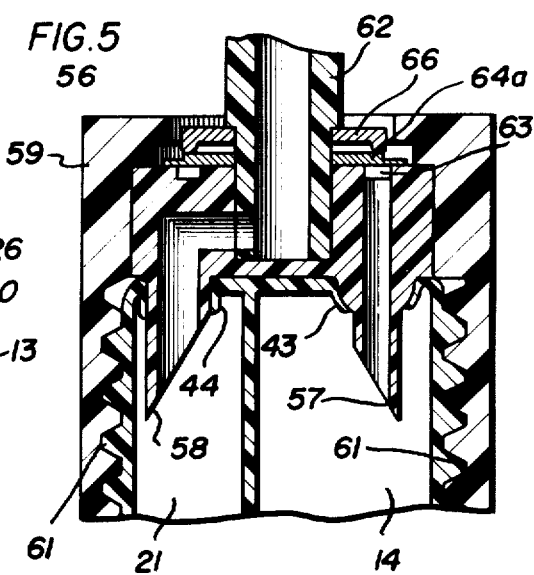
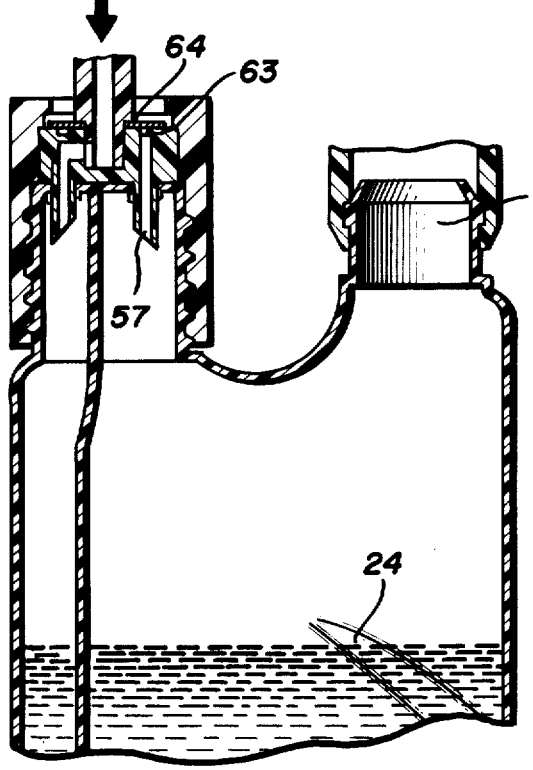
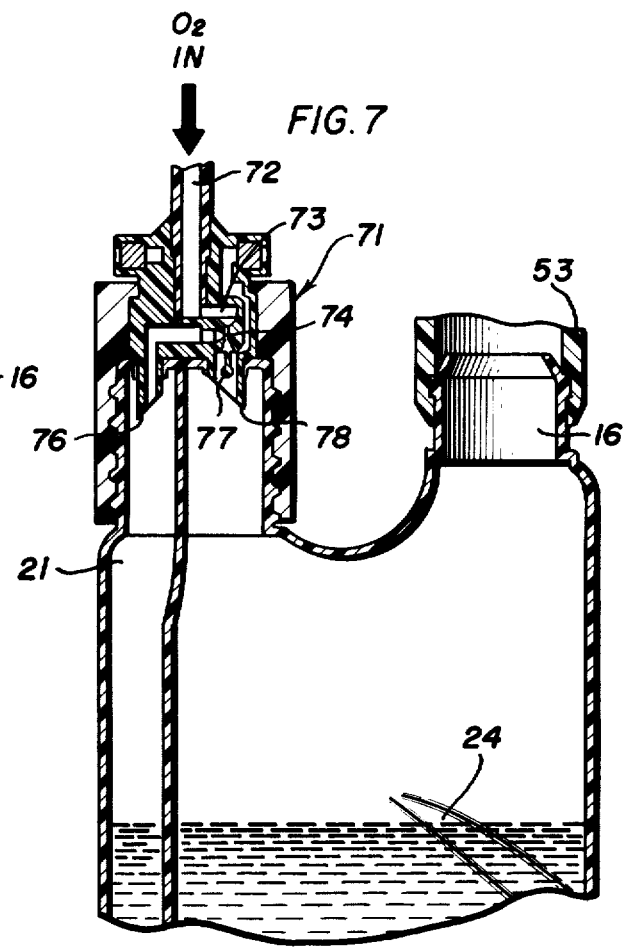

NEBULIZER-HUMIDIFIER SYSTEM

This is a continuation, of application Ser. No. 483,227, filed June 263 1974, now abandoned.

This invention relates to inhalation therapy, and more particularly to a combination humidifiernebulizer for introducing a liquid into an inhalable gas stream.

BACKGROUND OF THE INVENTION

In inhalation therapy, it is considered essential that the stream of gas, typically oxygen or air, be moisturized by the introduction of water vapor or nebulized particles of water prior to inhalation by a patient. Moisturization of the gas stream is usually accomplished by bubbling gas through a bath of water in a humidifier, or by nebulizing the water into extremely fine particles which are then transported by the gas into the lungs of the patient. In order to heat the gas stream to body temperature for the comfort of the patient and to aid in the vaporization of the water, it is customary to heat the water bath to the desired operating temperature, either indirectly by the application of heat to the container holding the water or directly by inserting a suitable heating element into the water bath. The time required to heat the entire water bath to operating temperature, however, entails an undesirable delay before the apparatus is ready for use, while the direct introduction of a heating element into the water creates the possibility of producing an unsterile condition. Moreover, if the apparatus is not disposable, use by different patients also creates the risk of transfer of infection.

BRIEF DESCRIPTION OF THE INVENTION

The present invention provides a device for use in inhalation therapy which can be used either as a humidifier or a nebulizer, with provision for heating the liquid when desired. The heat is applied indirectly to a relatively small volume of the liquid, thus quickly bringing it to operating temperature, so that the device is ready for use with a minimum of delay. In its preferred embodiment, the device of the invention is formed of inexpensive thermoplastic material which can be sealed to enclose a supply of sterile liquid, thereby maintaining sterile conditions, and which can be discarded after a single use to minimize the risk of infection.

The device comprises a container for liquid provided with inlet and outlet means and with a diffusion chamber defined in part by a horizontal perforated diffusion plate spaced above the bottom of the container. Two external conduits communicate with the diffusion chamber, a first conduit leading from the chamber to a point at the top of the container preferably near the inlet thereof, and a second conduit communicating with the interior of the container at an intermediate point in its height. The diffusion chamber is provided with external heating means and with means for closing the perforations in the diffusion plate when the heater is in use.

For use as a humidifier, gas is supplied to the container through the first conduit, the gas passing through the diffusion plate and/or the second conduit, bubbling through the liquid in the container and/or conduit, and leaving through the outlet in the top of the container. For use in nebulizing the liquid, a gas stream is introduced into the container through a venturi-type nebulizing head feeding into the inlet of the container, with the first conduit being used to aspirate liquid from the container and to supply it to the venturi. The stream of gas and nebulized liquid passes through the container in the vapor space above the liquid and emerges through the container outlet. Large particles of liquid fall into the liquid bath, while rain-out from the container outlet drops into the liquid in the vicinity of the inlet to the second conduit, and thence through the diffusion chamber, where it is heated if desired, and into the first conduit for another pass through the nebulizing head.

DESCRIPTION OF THE DRAWINGS

The invention will be better understood from the following detailed description thereof, taken in conjunction with the accompanying drawings, in which:

FIG. 1 is an isometric view of the device of the invention;

FIG. 2 is a vertical section through the embodiment of FIG. 1, showing also a removable heating assembly adapted to be inserted in the base of the container;

FIG. 3 is an exploded isometric view of a sub-assembly which can be used to form the diffusion chamber in the bottom of the container;

FIG. 4 is a sectional view along the line 4—4 of FIG. 1, showing the interior construction of the diffusion zone with the heater in place;

FIG. 5 is a vertical sectional view of a typical humidifier head in position at the inlet of the container;

FIG. 6 is a vertical sectional view of the upper portion of the container showing the humidifier head of FIG. 5 and the outlet of the container; and FIG. 7 is a view similar to that of FIG. 6 in which a nebulizer head is substituted for the humidifier head at the inlet to the container.

DETAILED DESCRIPTION

As shown in the figures, a typical embodiment of the invention comprises a container 10 having a top portion 11, a continuous side wall 12, and a bottom 13 which is sealed to the side wall. The container 10 is also provided with inlet means 14 and outlet means 16, through which the gas to be moisturized is introduced to the humidifier-nebulizer and withdrawn therefrom for delivery to a patient.

At the lower portion of the container 10, there is provided a chamber 17 defined by a perforated plate 18, the side wall 12 of the container, and bottom 13. Container 10 is also provided with two external conduits. First conduit 19 communicates at its lower end with diffusion chamber 17 and has an upper end 21 located in the vicinity of the inlet 14 to the container. Second conduit 22 similarly communicates with diffusion chamber 17 at its lower end, the upper end 23 of the second conduit being flared into the side wall 12 of the container, the joint forming an upwardly and outwardly extending generally horizontal deflecting surface 24.

FIG. 3 shows the elements of a sub-assembly which can be used to form part of diffusion chamber 17 in the base of the container. The upper element 26 of the sub-assembly is a hollow cup-shaped element, the top of which contains vertical perforations 27 and forms the gas diffusion plate 18 shown in FIG. 2. Upper element 26 further comprises a continuous sidewall 30. The lower element 28 provides the bottom 13 of container 10. Element 28 is provided with positioning notches 29 into which fit corresponding projections 31 in the rim of element 26. Connected to the bottom 13 of element 28 are a number of vertical ribs 32. One edge of cup element 26 is provided with a plurality of vertical openings 33 through which conduit 22 communicates with chamber 17. Diametrically opposite openings 33 in element 26 in open ports 34 through which conduit 19 communicates with chamber 17. It will be understood by those skilled in the art that chamber 17 may be of a size appropriate for the proposed use of the container 10. It is expected, for example, that a smaller chamber may be appropriate when a flow rate of gas of about 3 liters per minute is employed and a larger one may be appropriate with a flow rate of 10 liters per minute.

For ease in constructing the devices of the invention the sub-assembly shown in FIG. 3 can be fabricated from a preferred material, which is a thermoplastic resin such as polyethylene, polypropylene, or the like, or from metallic or fused plastic and metal materials. It should be understood, however, that the procedure used to make the container is not per se part of the invention, and any suitable fabrication method can be used. In the finished article, all contacting surfaces are sealed together to form an integral structure. In a preferred method of fabrication, hot thermoplastic materials forming the walls of container 10 are contacted with skirt rims 36a of skirt 36 of bottom 13 and trimmed away by knife along with rim 36a to obtain a tight seal in the final cooled container. As shown in FIG. 4, sidewall 12 substantially extends over and beyond sidewall 30 of the diffusion chamber. With the separate elements of FIG. 3 assembled and formed into the base of container 10, the resultant construction is one in which the lower outlet of first conduit 19 feeds the port 34 of the gas diffusion chamber 17, while the vertical openings 33 in the chamber are in fluid communication with the lower end of second conduit 22.

Skirt 36 which encircles the bottom 13 of container 10 is provided with internal threads 37 adapted to engage corresponding threads 28 on electrical heater assembly 39 which is provided with an upstanding circular heating surface 41. When heater assembly 39 is screwed into the threaded opening in skirt 36 of container 10, heating surface 41 comes into contact bottom 13, which is provided with a circular groove 42 surrounding ribs 32. Groove 42 acts as a bellows, and permits upward movement of heating surface 41 to cause bottom 13 to flex upwardly and to bring the top surfaces of ribs 32, normally spaced below plate 18, into contact therewith. The perforations 32 in plate 18 are aligned above the ribs, so that such contact effectively seals the perforations against fluid flow through diffusion plate 18. In order, however, to permit some liquid from the container to be able to enter diffusion chamber 17, one or more of the ribs, e.g. rib 32a, may be provided with an inclined upper surface 32b which does not effectively seal all of the perforation above it. Alternatively, one or more perforations may be provided in diffusion plate 18 which are not in a position to be sealed by the ribs when they are forced into contact with the plate.

The device shown in FIG. 2 provides a convenient, inexpensive and therefore disposable unit which can be pre-filled with a suitable quantity of fluid 40 such as sterile water, normal saline solution or solutions of medicaments such as isoetharine, phenylephrine, isoproterenol hydrochloride and the like, and sealed against the entry of contamination prior to use. For access to the interior of the container, sealed inlet 14 of the container is provided with ports 43 in which the wall thickness is reduced for easy penetration by a suitable adapter. The inlet 21 to conduit 19 is provided with a similar port 14.

The outlet 16 from container 10 is sealed with a cap 46 which provides exit ports of two different sizes depending on the intended use of the container. When a relatively small outlet is desired, tab 47 is pulled to remove cap 48 from nozzle 49, thus providing a relatively small nozzle fitting to which a suitable delivery hose can be affixed. When a larger outlet is desired, ring 51 is pulled, causing the fitting to separate at partition line 52, leaving an unimpeded full size outlet. A tube 53 for delivery of the moisturized gas from outlet 16 can be conveniently attached thereto by means of flange 54 which encircles the delivery opening.

For use as a humidifier, there is attached to the inlet 14 of container 10 an adapter 56, suitably of the form shown in FIG. 5, which is provided with pointed hollow projections 57 and 58 designed to penetrate the ports 43 and 44 in the inlets 14 and 21 to container 10 and to first conduit 19. The humidifier adatper is held by means of threaded cap 59 which engages mating threads 61 provided about both of inlets 14 and 21. A gap 60 can be provided between the inlet 21 to first conduit 19 and the inlet 14 to container 10 to accommodate a vertical positioning rod (not shown) in cap 59 which insures proper orientation of the humidifier adapter and also prevents rotation thereof. Conduit 62 supplies the gas to be humidified from a convenient source not shown.

The bore of projection 58 in the adapter communicates with conduit 62 supplying the gas and conveys the gas stream through first conduit 21 into gas diffusion chamber 17. The gas stream emerges from the gas diffusion chamber through the perforations 27 in plate 18, assuming that heater assembly 39 is not being used. A portion of the gas stream will also pass through grooves 33 in the side wall of the diffusion chamber and into second conduit 22. In passing through the supernatant layer of liquid above plate 18 or within conduit 22, the gas is humidified as desired and then passes through outlet 16 and delivery tube 53 to the patient.

When it is desired to heat the liquid in humidification, heater assembly 39 is screwed into position at the base of container 10, thereby lifting bottom 13 and causing ribs 33 to seal off perforations 27 in plate 18. Heat flowing by conduction through ribs 32 and bottom 13 in contact with heating surface 41 of the heater assembly 39 will warm the stream of gas passing through chamber 17 as well as liquid which is present in the chamber, so that the delivered stream of humidified air is at an elevated temperature. As long as the liquid level in container 10 remains above the mouth of second conduit 23, water can enter diffusion chamber 17 through second conduit 22. After a period of use, however, the liquid level may fall below the mouth of conduit 23 and accordingly no liquid would remain in the diffusion chamber or conduit 22. In order to prevent this situation, provision can be made to prevent seal of the perforations 27 in plate 18, so that a controlled flow of liquid to the diffusion chamber 17 will still occur even when the level of liquid within the container is low. This can be accomplished, as previously mentioned, by modifying a portion of one or more of ribs 32 so that some of the perforations in plate 18 always remain open.

In order to prevent the development of excessive pressure in container 10 which might result if delivery tube 53 is for any reason blocked, humidifier adapter 56 is provided with a pressure release valve communicating with projection 57, which communicates with the interior of container 10. As shown in FIG. 6, the upper end of the bore in projections 57 communicates with an annular groove 63 in the top surface of the adapter assembly. Groove 63 is sealed against fluid flow in normal operation by a flexible washer 64 which closes the top of the groove. In the event that excessive pressure develops within the interior of container 10, the force against the washer is sufficient to distort it and permit gas to escape from the groove around the outer periphery of the washer.

In a preferred embodiment of the release valve, shown in FIG. 5, provision is made for an audible signal that excessive pressure exists within container 10. As shown, washer 64a covering the top of annular groove 63 is held in place by a flexible hold-down member 66 bearing against its upper surface. The outer periphery of washer 64a is reduced in thickness, thus permitting it to flutter when sufficient pressure develops within container 10 to cause the gas to escape therefrom. The fluttering of washer 64a creates an audible signal to indicate the existence of excessive pressure.

FIG. 7 illustrates the use of the device of the invention in nebulizing a liquid such as water into a gas stream. The embodiment shown in FIG. 7 uses a nebulizer assembly 71 which is joined to conduit 21 and the inlet 14 to container 10 as shown in FIG. 5. Conduit 72 supplies a stream of gas and communicates through passage 73 to venturi 74. Projection 76 serves as a conduit for feeding the liquid to be nebulized to the venturi in conventional fashion. In operation, the stream of gas passing through the venturi aspirates a supply of liquid from container 10 up through first conduit 21. The liquid is fed into the gas stream and impinges on deflector element 77 within projection 78 causing the nebulization of the liquid into small particles. The stream of gas and nebulized liquid is fed into the vapor space of container 10 above the liquid level. Particles too large to be carried by the stream of gas fall into the body of liquid, while the finely-divided particles are carried in suspension in the stream of gas and exit through the outlet 16 of the container. Condensation or rain-out which occurs in the vicinity of outlet 16 or in delivery tube 53 can drop back into the container onto deflecting surface 24, which directs the rain-out back into second conduit 22 for another trip through the nebulizing head. If heated feeding of the nebulized stream is desired, heating assembly 39 can be inserted in the base of container 10 as previously described with respect to heating in connection with humidifying.

The result obtained in such a heating and nebulizing procedure is a most desirable one. Restriction of fluid flow through perforations 27 effectively establishes a separation between the principal body of fluid 40 within the upper, main portion of container 10 and the fluid within chamber 17. This tends to promote faster heating of fluid in chamber 17 immediately prior to its aspiration to the nebulizing head and avoids the necessity of heating all of the fluid in the container prior to nebulizing activity. Further, warmed rain-out derived from the vicinity of outlet 16 is substantially directed back toward chamber 17 through conduit 22 rather than toward the principal body of fluid 40, thus essentially providing a "pre-warmed" source of fluid to be heated prior to nebulization and giving rise to a savings of heating time and energy.

The foregoing detailed description has been given for clearness of understanding only, and no unnecessary limitations should be understood therefrom, as modifications will be obvious to those skilled in the art.

What is claimed is:

1. An inhalation therapy device for use either in a first, humidifying, or a second, nebulizing, therapeutic mode for delivery of a moisturized gas stream to a patient, said device comprising:
    container means for containing a gas stream-moisturizing liquid, said container means including
    1. a top element,
    2. a bottom element,
    3. a continuous sidewall element interconnecting said top and bottom elements,
    4. perforated gas stream-diffusing plate means spaced above said bottom element within said container means and defining with said bottom element and said sidewall element a gas stream diffusion chamber within said container means,
    5. means in said top element providing a delivery outlet for a moisturized gas stream from within said container means, and
    6. passage means in said top element providing
        a. an outlet for exhausting a gas stream from said container means upon blockage of said delivery outlet means when the device is employed in said first therapeutic mode and
        b. an inlet for entry of a moisturized gas stream into said container means when the device is employed in said second therapeutic mode; and
    conduit means for fluid flow, communicating between said diffusion chamber and a point at said top of said container means adajcent said passage means, and providing
        a. a gas stream conduit when the device is employed in said first therapeutic mode and
        b. a liquid conduit when the device is employed in said second therapeutic mode.

2. A device according to claim 1 further including a second conduit means for fluid flow formed integrally with said sidewall, said second conduit means communicating between said diffusion chamber and said container means and discharging within said container means at an elevation above said diffusion chamber and below said top element.

3. A device according to claim 2 in which said second conduit joins said sidewall in a flaring connection located directly beneath said delivery outlet means, said flaring connection comprising an inclined deflecting surface adapted to direct liquid dropping into said container from said delivery outlet means into said second conduit.

4. A device according to claim 1 in which said diffusion chamber is provided with heating means for heating fluid passing therethrough, said heating means comprising a plurality of vertical fins joined to said bottom element and spaced from the perforations in said plate means, said bottom element being adapted to receive an external heater which heats said bottom element and said fins attached thereto by conduction.

5. A device according to claim 4 in which said bottom element is flexible and is adapted to be raised by contact with said heater relative to said diffusion plate means, whereby said fins restrict the perforations in said plate means against the flow of fluid therethrough.

6. A device according to claim 1 containing a supply of volatile liquid for gas stream moisturization, said passage means, delivery outlet means and conduit means being sealed against the escape of said liquid from said container means.

7. A device according to claim 6 in which said liquid is water.

8. A device according to claim 6 further including sealing means for said delivery outlet means selectively breachable to form exit ports of differing sizes.

9. A device according to claim 1 further including adapter means for use in operating the device within said first therapeutic mode, said adapter means comprising means for supplying a gas stream to said conduit means and means for open communication between the interior and exterior of said container means through said passage means.

10. A device according to claim 1 further including adapter means for use in operating the device within said second therapeutic mode, said adapter means comprising mist-forming means adapted to be secured to said passage means and conduit means, said mist-forming means including a gas stream inlet, and inlet for liquid to be nebulized from said conduit means, and an outlet for directing said gas stream and liquid nebulized by said mist-forming means through said passage means into said container means.

11. In a container apparatus for administering a fluid in the course of inhalation therapy, said container apparatus including a chamber having a lower portion and fluid conduit means for delivery of said fluid to said lower portion, the improvement comprising:

a diffusion chamber sub-assembly comprising:

a. a perforated upper part;

b. a lower part;

c. a substantially continuous sidewall between said upper and lower parts;

d. said sidewall including orifice means for entry of said fluid;

said container chamber having a substantially continuous sidewall including a lower portion which contacts and overlies said sub-assembly in fluid-sealing relationship; and said orifice means being in fluid communication with said fluid conduit means to facilitate the flow of said fluid from said fluid conduit means to said diffusion chamber for dispersion of said fluid through said perforated upper part and into said chamber.

12. The improvement as set forth in claim 11 wherein said chamber and said fluid conduit means comprises thermoplastic material.

* * * * *